United States Patent
Drachmann et al.

(10) Patent No.: US 6,712,070 B2
(45) Date of Patent: Mar. 30, 2004

(54) INHALATION DEVICE

(76) Inventors: Bo Drachmann, Sankt Annae Gade 18, 1416 København K (DK); Per Andersen, Snerlehaven 61, 2630 Taastrup (DK)

(*) Notice: Subject to any disclaimer, the term of this patent is extended or adjusted under 35 U.S.C. 154(b) by 170 days.

(21) Appl. No.: 09/991,981

(22) Filed: Nov. 26, 2001

(65) Prior Publication Data

US 2003/0098023 A1 May 29, 2003

(51) Int. Cl.$^7$ .............................................. A61M 16/10
(52) U.S. Cl. ......................... 128/203.12; 128/200.23; 128/203.15; 128/203.16
(58) Field of Search ................... 128/200.23, 203.12, 128/203.15, 203.23, 200.14, 200.16, 200.18; 604/58

(56) References Cited

U.S. PATENT DOCUMENTS

| | | | | |
|---|---|---|---|---|
| 3,101,905 | A | * 8/1963 | Hoenig | ........................ 239/357 |
| 4,534,343 | A | 8/1985 | Nowacki et al. | |
| 5,042,467 | A | 8/1991 | Foley | |
| 5,103,854 | A | * 4/1992 | Bailey et al. | ................ 137/102 |
| 5,571,246 | A | * 11/1996 | Alldredge | .............. 128/200.23 |
| 5,746,197 | A | * 5/1998 | Williams | ................ 128/200.23 |
| 5,816,240 | A | 10/1998 | Komesaroff | |
| 6,039,042 | A | 3/2000 | Sladek | |
| 6,293,279 | B1 | 9/2001 | Schmidt et al. | |
| 6,363,932 | B1 | * 4/2002 | Forchione et al. | ..... 128/203.12 |

FOREIGN PATENT DOCUMENTS

| | | | | |
|---|---|---|---|---|
| EP | 0 938 908 | | 9/1999 | |
| EP | 938908 | A2 * | 9/1999 | .......... A61M/15/00 |
| GB | 2 293 110 | | 3/1996 | |
| WO | WO 98/31411 | A1 | 7/1998 | |
| WO | WO 00/64520 | A1 | 11/2000 | |

* cited by examiner

Primary Examiner—Henry Bennett
Assistant Examiner—Amanda Flynn
(74) Attorney, Agent, or Firm—Burns, Doane, Swecker & Mathis, L.L.P.

(57) ABSTRACT

The invention concerns a device (1) for the inhalation of at least one drug from a gas canister (98) having a nozzle (96) by a person suffering from asthma or bronchospasm, the device comprising a gas container (10) having at least one wall (12), the wall surrounding a gas containment chamber (14) adapted to contain gas at a pressure larger than atmospheric pressure, the gas container (10) further having an inlet (16) adapted for connection to the nozzle (96) of the gas canister (98), the gas container (10) further having an outlet (18) with an outlet valve (20) adapted to allow the person to inhale gas from the device through the outlet; wherein the outlet valve (20) is adapted to be activated by the inhalation of the person independent of the activation of the gas canister (98). This invention allows the person to activate the gas canister, and pause before inhalation. The invention is adapted to facilitate coordination for the patient inhaling.

19 Claims, 3 Drawing Sheets

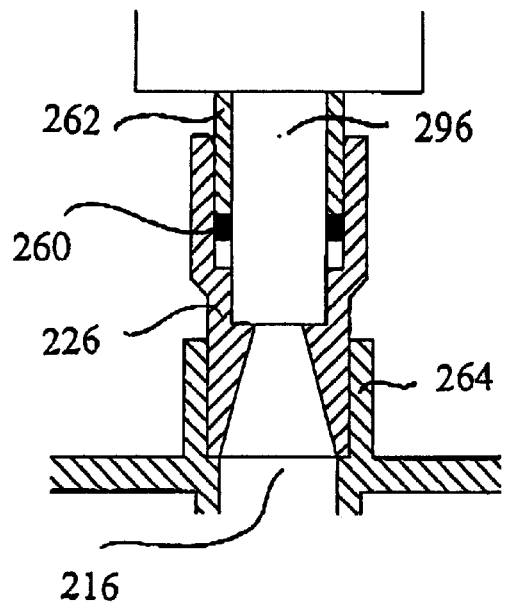
Fig. 4
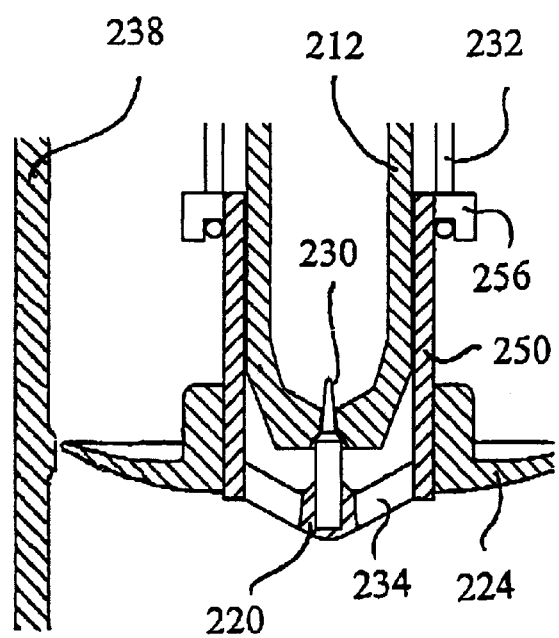
Fig. 6
Fig. 5

INHALATION DEVICE

TECHNICAL FIELD

The present invention concerns a gas inhalation device and its use. The invention in particular concerns a gas inhalation device, which is breath-activated, for use with a gas canister and the use of the gas inhalation device.

TECHNICAL BACKGROUND

A basic purpose of many inhalation devices is to provide means for ensuring the administration of a drug in a way establishing physical contact between the drug and the airways, and preferably the lower airways or fine receptors of the lungs, of a patient to be treated. Note that while the present invention was developed with asthma inhalation devices in mind, the present devices may naturally be used for administration of drugs for other diseases.

Two technologies are in widespread use in asthma inhalation devices. One is powder based, the other is gas canister based. Powder devices suffer from the drawback that the particle sizes used are relatively large, making it difficult for them to reach the fine receptors of the lungs. Gas devices provide finer particles, but eject these at a relatively high speed. A typical gas device will by activation in air create a small cloud having a length of typically 30–40 cm. On use such a cloud is likely to get in physical contact with the inner part of the mouth, i.e. the palate, rather than the fine receptors of the lungs where it is intended. A short description of the airways may elucidate this point. The upper airways include the oropharynx and larynx. The lower airways start in the trachea, which is followed by successive bifurcation into bronchi and bronchioli. Down to this point, the spaces are called conductive airways. The terminal bronchioli then divide into respiratory bronchioli until the ultimate respiratory zone, the alveoli, is reached. There is a very steep increase in the surface area with successive airways generations with consequences for drug absorption.

The inventors of the present invention have realized, that a problem occuring with the use of the known gas inhalation devices is achieving an appropriate speed of drug on inhalation. If the speed is too high, a high proportion of the drug is shot directly into the roof of the mouth, i.e. the palate. If the speed is too slow only a small portion of the drug will make it to the fine receptors of the lungs. It is usually regarded desirable to provide a large percentage of the drug in physical contact with the fine receptors of the lungs, i.e. increasing the contact area between drug and alveoli.

As an example of a powder inhaler WO 00/64520 describes a device for two or more medicaments. The powder is administered to the patient when the patient sucks from the mouthpiece and inhales the powder.

As an example of a gas canister based device EP 0 311 770 B1 describes a respiratory therapy device with a large aerosol vortexing chamber. This patent describes the beneficial effects of using a slow aerosol flow. Administration is performed when the patient inhales from a mouthpiece through a valve from the large aerosol vortexing chamber.

Another problem associated with known inhalation devices is that many of them demand coordination of breathing rhythm, activation of the device and application of the device to the mouth of the patient. Such coordination may be difficult, especially for a patient struggling to get air, and for children and aged people. It is desirable to facilitate such coordination in order to optimise administration of the drugs.

According to an aspect of the present invention it is an object of the present invention to provide means for enhancing the probability of a therapeutically effective amount of active substance reaches the fine receptors of the lungs.

According to another aspect of the present invention it is an object of the present invention to provide means for allowing a patient and/or an attending physician to achieve better control of the inhalation process and/or the way a drug is administered.

Some desirable aspects of asthma devices provided according to the present invention may be summarized as: high percentage of drug administered to patient; adequate, adjustable speed of gas on inhalation; easy adjustment of pressure without need of changing gas canister (e.g. by multiple activation of gas canister); utility with many existing gas canisters on the market; portability of device, due to size and design; discrete design; easy use, low price of device; and/or secure locking mechanism to prevent unwanted release of gas.

DISCLOSURE OF THE INVENTION

The present invention concerns a device for the inhalation of at least one drug, from a gas canister having a nozzle, by a person suffering from asthma or bronchospasm, said device comprising: a gas container having at least one wall, said wall surrounding a gas containment chamber adapted to contain gas at a pressure larger than atmospheric pressure, said gas container further having an inlet adapted for connection to the nozzle of the gas canister, said gas container further having an outlet with an outlet valve adapted to allow the person to inhale gas from said device through said outlet; wherein said outlet valve is adapted to be activated by the inhalation of the person independent of the activation of the gas canister.

This aspect allows the person to activate the gas canister, and pause before inhalation. Gas from the gas canister will be contained in the gas containment chamber at a pressure larger than atmospheric pressure. On inhalation the outlet valve may be activated. The gas contained in the gas containment chamber will expand rapidly and enter the airways of the person on activation of the outlet valve. Thus, this aspect may facilitate coordination for the patient inhaling. This encourages the patient to perform a slow, deep inhalation, for maximum deep-lung delivery of the active substance (drug).

Existing, commercially available gas canisters, which may be used with the present invention, are usually provided with a nozzle. Activation of the gas canister is done by pressing or forcing the nozzle in direction towards the gas canister, whereby a dose of active drug is emitted from the nozzle. A usual gas canister contains propellant for a higher number of doses than the number of doses of active drug in the gas canister. A vent inside the gas canister ensures that an approximately constant volume of active drug is administered on each activation of the gas canister, until the active drug has been used. The gas canisters may be any suitable gas ganisters, and inter alia contain drugs such as Bricanyl, Salbutamol, and Beclometasom.

The device according to the invention may be made from any suitable material, inter alia from metal or plastic by e.g. molding, casting or lathing. Especially preferred materials are discussed below.

DETAILED DISCLOSURE

The invention further concerns a device comprising a mouthpiece adapted to allow the person to inhale from said mouthpiece, said mouthpiece being in flow communication with said outlet valve. A mouthpiece facilitates the inhalation through the mouth of the patient.

The invention further concerns a device provided with a removable spacer for said mouthpiece, said spacer allowing extending said mouthpiece on mounting. Some patients prefer to have such a spacer inserted on use, and such a spacer may be recommended for children and aged people.

The invention further concerns a device comprising an exhalation valve; wherein said mouthpiece is in flow communication with said exhalation valve, allowing the person to exhale through the mouthpiece. This aspect further facilitates coordination of activation of gas, exhalation and subsequent inhalation of active substance, as it is not necessary to remove the mouth from the mouthpiece when exhaling.

The invention further concerns a device, wherein said inlet is provided with receiving means being connectable to said inlet of said gas container, wherein said receiving means is adapted to receive the nozzle of the gas canister. This aspect may allow easy adaptation to different gas canisters, simply by changing the receiving means according to the selected gas canister.

The invention further concerns a device having gas canister holding means connected to said gas container, said gas canister holding means being adapted to receiving and holding the gas canister. This aspect ensures stable, secure mounting of the gas canister.

The invention further concerns a device; wherein the atmosphere surrounding said device has a pressure, $P_{atm}$, said outlet valve experiences an inner pressure from said gas containment chamber before activation of said outlet valve, $P_{ca}$; and said outlet valve experiences an outer pressure before activation of said outlet valve, $P_{ma}$; wherein said outlet valve is adapted to have an outlet valve parameter, OVP, larger than 1; said outlet valve parameter, OVP, being defined by the condition for activation, B, of said outlet valve:

$$B: |P_{ca}-P_{atm}|-OVP|P_{atm}-P_{ma}|<0 \; atm;$$

such that said outlet valve of said container is activated when said condition for activation, B, is fulfilled.

This aspect allows a small under pressure, with respect to atmospheric pressure, created by the patient, to be sufficient to activate the outlet valve, while a large overpressure, with respect to atmospheric pressure, in the gas containment chamber, does not activate the outlet valve. For the parameter OVP being larger than 1 the outlet valve is activated by a smaller underpressure in e.g. the mouthpiece, rather than by a larger overpressure in the gas containment chamber. The parameter OVP may be adjusted e.g. by altering the design of the outlet valve.

The parameter OVP for a given device according to the invention may be measured by filling the gas containment chamber with gas at a given pressure, $P_{ca}$, e.g. with a gas canister. Subsequently, the pressure, $P_{ma}$, exerting a force on the outside of the outlet valve is lowered slowly, while measuring this pressure, $P_{ma}$. When the valve is activated by the pressure difference across the outlet valve, the parameter OVP may to a good approximation be calculated as:

$$OVP \approx |P_{ca}-P_{atm}|/|P_{atm}-P_{ma}|.$$

The slower the pressure $P_{ma}$ is lowered, the more accurate measurement of OVP may be achieved.

In order to elucidate the significance of the OVP parameter we offer an example below. Assume a device according to the invention has an OVP=2. The pressure surrounding the device is about 1 atm. Further assume that activation of the gas canister raises the pressure to 1.3 atm inside the gas containment chamber. Before the patient inhales from the device the outer pressure, which the outlet valve experiences, is about 1 atm. Thus, we see that the condition for activation $$B: |P_{ca}-P_{atm}|-OVP|P_{atm}-P_{ma}|<0 \; atm$$

is not fulfilled, by inserting:

$$|1.3-1|-2*|1-1|=0.3 \; (atm).$$

Now, when the patient begins to inhale, the $P_{ma}$ is lowered. We see that $P_{ma}<0.85$ is necessary to activate the outlet valve, as for $P_{ma} \approx 0.85$ atm:

$$|1.3-1|-2*|1-0.85|=0.0 \; (atm).$$

Evidently, higher values of the OVP parameter are desirable, if it is wanted that the outlet valve should be easier to activate for the patient. The higher the value, the less pressure has to be lowered on inhalation, in order to activate the outlet valve. As another example assume OVP=500, while the rest of the conditions listed above remain unchanged. We see that:

$$|1.3-1|-500*|1-0.9994|=0.0 \; (atm),$$

i.e. $P_{ma}<0.9994$ is sufficient for activating the outlet valve.

One way to achieve an OVP parameter larger than 1 is to allow the outer pressure to exert a force on a larger area of the outlet valve, than the area of the outlet valve, which the gas in the gas containment chamber is allowed to exert a force on. Thus, the outlet valve may have a large area, with respect to the patient, and a small area, with respect to the gas containment chamber.

The invention further concerns a device, wherein said outlet valve is adapted to have an outlet valve parameter, OVP, larger than a number selected among the group consisting of 20; 15; 10; 8; 6; 5; 4; 3; 2.5; 2; 1.5; 1.4; 1.3; 1.2 and 1.1. The appropriate choice of the parameter OVP may be obtained easily by routine experiment and adapted to the preferences of the patient.

The invention further concerns a device, wherein said outlet valve comprises a valve pin, spring means and spring attachment means; said spring means being connected to said gas container, and via said spring attachment means being connected to and forcing said valve pin to close said outlet valve except on inhalation, and allowing said outlet valve to open upon inhalation.

A pressure pin allows a small underpressure in the mouthpiece to activate the outlet valve, while the outlet valve is not activated by a larger than atmospheric pressure in the gas containment chamber.

The invention further concerns a device, wherein said spring means are rubber bands. Alternatively a metallic, plastic or rubber spring may be used.

The invention further concerns a device, wherein the gas in said gas containment chamber exerts a force on said outlet valve on a first area, $A_1$, and the outer pressure exerts a force on the outlet valve on a second area, $A_2$, said first area being smaller than said second area; $A_1<A_2$. This aspect may provide a parameter, OVP, larger than 1.

The invention further concerns a device, wherein the ratio, $A_2/A_1$, between said second area, $A_2$, and said first area, $A_1$, is larger than a number selected among the group consisting of 5000; 2000; 1500; 1000; 500; 300; 100; 50; 30;

20; 10; 5; 4; 3; 2 and 1.5. The larger the ratio, the easier it will be to inhale gas from the device. Thus, this aspect facilitates inhalation.

The invention further concerns a device, said device comprising an outer wall and spacing means for connecting said gas container with said outer wall; wherein said outlet valve comprises an exhalation valve having a resilient flap valve with a circumference in close proximity to said outer wall, said resilient flap valve being adapted to allow air to be exhaled without activation of said outlet valve, and allowing activation of said outlet valve upon inhalation; and said resilient flap valve having an inhalation opening through which gas from said gas containment chamber may pass, allowing gas to flow from the gas containment chamber to the patient upon inhalation.

This aspect provides a simple valve allowing both inhalation and exhalation with the device. The resilient flap valve may be made of e.g. rubber or plastic. Especially preferred is the material silicone.

The invention further concerns a device, wherein the force necessary to bend said resilient flap valve in direction towards the person is larger than the force necessary to bend said resilient flap valve in direction away from the person. This aspect provides easy exhalation through the resilient flap valve, and easy activation of the outlet valve upon inhalation.

The invention further concerns a device, wherein at least part of the resilient flap is convex with respect to the person. This aspect may provide easy exhalation through the resilient flap valve, and easy activation of the outlet valve upon inhalation.

The invention further concerns a device, wherein at least part of the resilient flap is concave with respect to the direction of the gas canister. This aspect may further provide easy exhalation through the resilient flap valve, and easy activation of the outlet valve upon inhalation.

The invention further concerns a device, wherein said resilient flap valve allows air to flow substantially freely on exhalation, while only allowing a limited stream of air to pass between said circumference of said resilient flap valve and the inner surface of said outer wall upon inhalation. The rigidity and dimensions of the resilient flap is easily adjusted by the person skilled in the art to achieve this. This may provide for a gas cloud which is limited and does not broaden too much.

The invention further concerns a device, said device comprising sliding means connected to said outlet valve, said sliding means being adapted to slide with respect to the outer surface of said wall of said gas container upon activation of said outlet valve. This aspect may help keeping the outlet valve functioning correctly, as it ensures correct location of the different parts of the outlet valve upon opening and closing.

The invention further concerns a device, wherein said sliding means surrounds said outer surface of said wall of said gas container completely, in a substantially air tight way. This aspect may hinder gas from escaping out in a direction different from the direction of the airways of the person.

The invention further concerns a device, said device comprising an outer will shaped as a tube with a diameter substantially equal to the diameter of the gas canister, said outer wall surrounding said inlet and said outlet of said gas container, and said device comprising spacing means for connecting said gas container with said outer wall; wherein said outer wall is connected to said mouthpiece.

A circular cross section of the device avoids sharp corners. Other suitable shapes are substantially oval, rectangular, or quadratic cross section, for allowing placement of the device on a surface without unintended rolling.

The invention further concerns a device, wherein said outer wall further surrounds at least part of the gas canister. This aspect conceals and supports the gas canister.

The invention further concerns a device, wherein said outer wall is provided with at least one opening situated between said inlet and said outlet of said gas container, for allowing air to be let out of the device upon exhalation. According to this aspect the patient may exhale through the mouthpiece.

The invention further concerns a device, said device comprising an outer cover, said outer cover covering at least part of the bottom part of the gas canister, wherein said cover is adapted as to closely fit the gas canister and allow movement of said outer cover with respect to said gas container, such that the gas container may be activated by movement of said cover. This aspect will cover at least part of the gas canister, thereby providing a more discreet look of the device.

The invention further concerns a device, wherein said outer cover is provided with a clip allowing fixation of the device to clothes. Suitable materials for such a clip are resilient materials, e.g. metal or plastic.

The invention further concerns a device, wherein the gas canister is activated by rotation of said outer cover with respect to said gas container. This aspect provides easy activation of the gas canister, while minimizing the risk of accidental activation when not intended.

The invention further concerns a device, wherein the outer cover comprises an elongated opening, said elongated opening having at least a part slanted with respect to the longitudinal direction of the gas canister, and said device further comprises an activation pin connected to said gas container, said pin engaging said elongated opening so that rotation of said outer cover with respect to said gas container activates said gas canister.

This aspect may be achieved by allowing a pin connected to the gas canister to stick through an at least partly helix shaped opening in a cover for the gas ganister. Rotation of the cover may then force the gas canister to be moved towards the mouthpiece.

The invention further concerns a device, wherein the outer surface of said device is shaped as a cylinder. This aspect may provide an inhalation device of convenient shape and size, which may look like an ordinary thick pen. Thus, a user may carry the device without attracting unwanted attention, as what might appear to be a pen is really an "Asthmapen".

The invention further concerns a device, wherein the gas containment chamber is adapted to contain gas at a pressure larger than a pressure selected among the group consisting of 1.05; 1.1; 1.2; 1.3; 1.5; 1.6; 1.7; 1.8; 1.9; 2; 2.5 and 3 atm.

Appropriate choice of the selected pressure will inter alia depend on the size of the gas containment chamber, the pressure of the gas canister, and the choice of valves. An appropriate choice of this pressure will help ensure a large fraction of drug reaches the fine receptors of the lungs. The pressure may be selected according to the needs of the individual patient.

The invention further concerns a device, wherein the gas containment chamber is adapted to contain gas at a pressure smaller than a pressure selected among the group consisting of 4; 3; 2.5; 2; 1.5; 1.4; 1.3; 1.2 and 1.1 atm. It may be desirable to avoid very large pressures, in order not to get a large fraction of drug adhered to the palate.

The invention further concerns a device, wherein the gas containment chamber has dimensions which reduces the speed of gas leaving the chamber to a fraction of the speed of gas entering the chamber.

According to an aspect of the present invention the present device is used for slowing the speed of gas from the gas canister before entering the mouth of the patient, in order not to get a large fraction of drug adhered to the palate.

The invention further concerns a device, where the gas containment chamber has dimensions which reduces the speed of gas leaving the chamber to a fraction of the speed of gas entering the chamber, said fraction being smaller than a number selected among the group consisting of 0.9; 0.8; 0.7; 0.6 and 0.55. Appropriate selection of this fraction may ensure high probability of a therapeutically effective amount of drug reaching the fine receptors of the lungs.

The invention further concerns a device, wherein the gas containment chamber has dimensions which reduces the speed of gas leaving the chamber to a fraction of the speed of gas entering the chamber, said fraction being larger than a number selected among the group consisting of 0.1; 0.2; 0.3; 0.4 and 0.45. Appropriate selection of this fraction may ensure high probability of a therapeutically effective amount of drug reaching the fine receptors of the lungs.

The invention further concerns a device, wherein the gas containment chamber has dimensions which reduces the speed of gas leaving the chamber to a fraction of the speed of gas entering the chamber, said fraction being selected among the group consisting of the intervals 0.9–0.1; 0.8–0.2; 0.7–0.3; 0.6 –0.4 and 0.55–0.45. Appropriate selection of this fraction may ensure high probability of a therapeutically effective amount of drug reaching the fine receptors of the lungs.

The invention further concerns a device, wherein the gas containment chamber has a volume with dimensions of the same order as the dimensions of the vent chamber inside the gas canister. Preliminary experiments indicate that such dimensions are appropriate to achieve a relatively large proportion of drug comes in contact with the fine receptors of the lungs.

The invention further concerns a device, wherein the gas containment chamber has a volume larger than a volume selected among the group consisting of 0.1 $cm^3$; 0.2 $cm^3$; 0.3 $cm^3$; 0.4 $cm^3$; 0.5 $cm^3$; 0.6 $cm^3$; 0.7 $cm^3$; 0.8 $cm^3$; 0.9 $cm^3$ and 1 $cm^3$. Preliminary experiments indicate that such dimensions are appropriate to achieve a relatively large proportion of drug comes in contact with the fine receptors of the lungs.

The invention further concerns a device, wherein the gas containment chamber has a volume smaller than a volume selected among the group consisting of 100 $cm^3$; 50 $cm^3$; 25 $cm^3$; 10 $cm^3$; 5 $cm^3$; 3 $cm^3$; 2 $cm^3$; 1.7 $cm^3$ and 1.5 $cm^3$.

The invention further concerns a device, wherein the gas containment chamber has a volume selected among the group consisting of the ranges 0.1–100 $cm^3$; 0.2–50 $cm^3$; 0.3–25 $cm^3$; 0.4–10 $cm^3$; 0.5–5 $cm^3$; 0.6–3 $cm^3$; 0.7–2 $cm^3$; 0.9–1.7 $cm^3$ and 1–1.5 $cm^3$.

Preliminary experiments indicate that the dimensions mentioned above are appropriate to achieve a relatively large proportion of drug comes in contact with the fine receptors of the lungs.

The invention further concerns a device, provided with removable cover means for covering said outlet valve, when said device is not used for inhalation. This aspect may provide protection of the outlet valve, when the device is not being used.

The present invention further concerns the use of the device according to the invention, wherein the gas canister is activated before inhalation. This aspect may facilitate coordination upon inhalation.

The invention further concerns a use, wherein multiple activations of the gas canister are performed before inhalation. This may provide a higher dose or higher pressure in the gas containment chamber. The pressure in the gas containment chamber will not exceed the pressure of the gas canister. Thus, easy, approximately constant dosing is possible.

The invention further concerns a use, wherein exhalation through a mouthpiece precedes inhalation through said mouthpiece. This aspect may facilitate coordination upon exhalation and subsequent inhalation.

DRAWINGS

Short Description of the Figures

FIG. 4 is a scale drawing of a part of the cross section shown in FIG. 2.

FIG. 5 is a scale drawing of a part of the cross-section shown in FIG. 2.

FIG. 6 is a section of the scale drawing of FIG. 2.

List of Reference Numerals

FIG. 1

Figure 1:
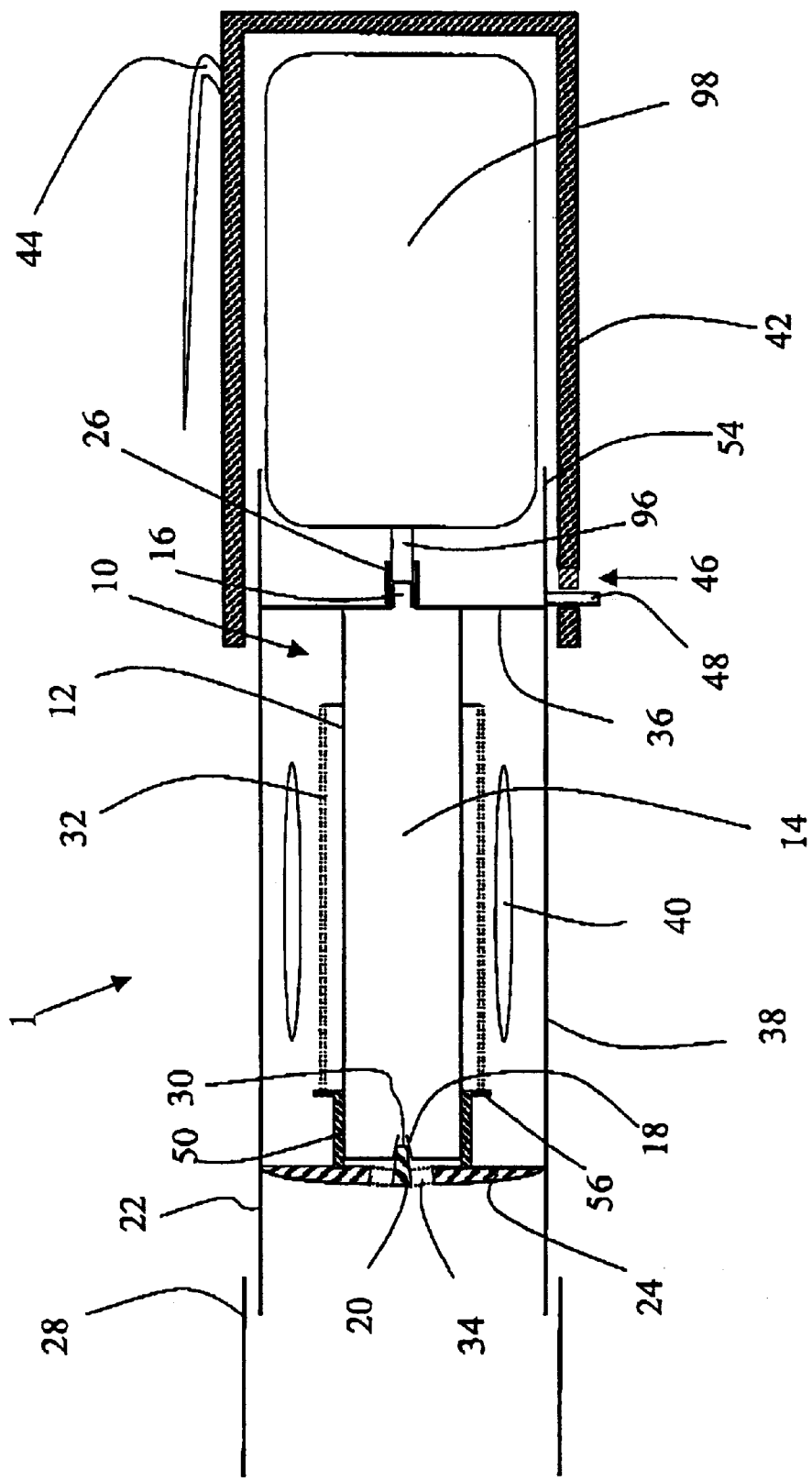
FIG. 1 is a schematic diagram of an embodiment of the present invention.

1 device
10 gas container
12 wall (of gas container)
14 gas containment chamber
16 inlet (of gas container)
18 outlet
20 outlet valve
22 mouthpiece
24 exhalation valve
26 receiving means
28 spacer
30 valve pin
32 spring means
34 inhalation opening
36 spacing means
38 outer wall
40 opening
42 outer cover
44 clip
46 elongated opening
48 activation pin
50 sliding means
54 gas canister holding means
56 spring attachment means
96 nozzle (of gas canister) [not part of the invention]
98 gas canister [not part of the invention]

FIGS. 2–6

201 device
210 gas container
212 wall (of gas container)
214 gas containment chamber
216 inlet (of gas container)
218 outlet 220 outlet valve
222 mouthpiece
224 exhalation valve
226 receiving means
228 spacer
230 valve pin
232 spring means
234 inhalation opening
236 spacing means
238 outer wall
240 opening
241 opening
242 outer cover
244 clip
246 elongated opening
248 activation pin
250 sliding means
252 cover means
254 gas canister holding means
256 spring attachment means
260 O-ring
262 sealing means
264 connecting part
296 nozzle (of gas canister) [not part of the invention]
298 gas canister [not part of the invention]

DETAILED DESCRIPTION OF THE FIGURES

FIG. 1 is a schematic diagram of an embodiment of a device 1. The device 1, adapted for inhalation of drug from a gas canister 98 by a person suffering from asthma or bronchospasm, comprises a gas container 10 with at least one wall 12. The wall 12 surrounds a gas containment chamber 14. The gas container 10 further has an inlet 16, adapted for connection to an outlet or nozzle 96 of the gas canister 98. The gas container 10 is provided with an outlet 18 with an outlet valve 20. The gas containment chamber 14 may be filled with gas on activation of the gas canister 98. The person may activate the outlet valve 20 on inhalation, whereby inhalation of the gas from the gas containment chamber 14 is possible. The mouthpiece 22, connected to the device 1, allows the person to inhale with the mouth directly from the device. The device 1 is further provided with a removable spacer 28 for said mouthpiece 22, whereby the mouthpiece 22 is effectively extended. The device has an exhalation valve 24, which is in flow communication with the mouthpiece. The person may exhale through the device, without loss of gas from the gas containment chamber 14. The inlet 16 is connected via receiving means 26 to the nozzle 96 of the gas canister 98. The receiving means 26 may be replaced, inter alia for easy adjustment of the device 1 to different types of gas canisters. Further the device 1 has gas canister holding means 54, for secure mounting of the gas canister. The outlet valve comprises a valve pin 30, spring means 32 and spring attachment means 56. The spring means 32 are connected to the gas container 10 and via the spring attachment means 56 to the valve pin 30. The spring means 32 force the valve pin 30 to close the outlet valve 20 except on inhalation, and allows the outlet valve 20 to open upon inhalation. The device 1 has an outer wall 38 and spacing means 36 for connecting the gas container 10 with the outer wall 38. The outlet valve 20 comprises the exhalation valve 24 with a resilient flap valve. The circumference of the resilient flap valve is in close proximity with the outer wall 38. The resilient flap valve has at least one inhalation opening 34 close to the center. This inhalation opening 34 allows gas to pass from the gas containment chamber to the patient upon inhalation. The device 1 has sliding means 50 around the wall 12 of the gas container 10. The sliding means can slide with respect to the outer surface of the wall 12 of the gas container 10, and is connected to the outlet valve 20, whereby the outlet valve will be held in place upon exhalation and inhalation. The outer wall 38 is shaped as a tube with a diameter substantially equal to the diameter of the gas canister. The outer wall 38 surrounds said inlet and said outlet of the gas container 10, and is connected to the gas container by the spacing means 36, as well as to the mouthpiece 22. The outer wall 38 is provided with a number of openings 40, situated between said inlet and said outlet of said gas container, whereby gas may escape upon exhalation. The device is further provided with an outer cover 42, which covers the gas canister. On the outside of the outer cover 42 is placed a clip 44, for fixation of the device 1 to clothes. The outer cover 42 has an elongated opening 46 through which a pin 48, attached to the device 1, protrudes. This makes it possible to effectuate activation of the gas canister 98 by rotation of the outer cover 42 with respect to the rest of the device 1. The outer surfaces of the device are generally cylinder shaped, which means the device mimics a normal thick pen.

Best Mode

Below, an especially preferred embodiment of the present invention will be described.

Figure 2:
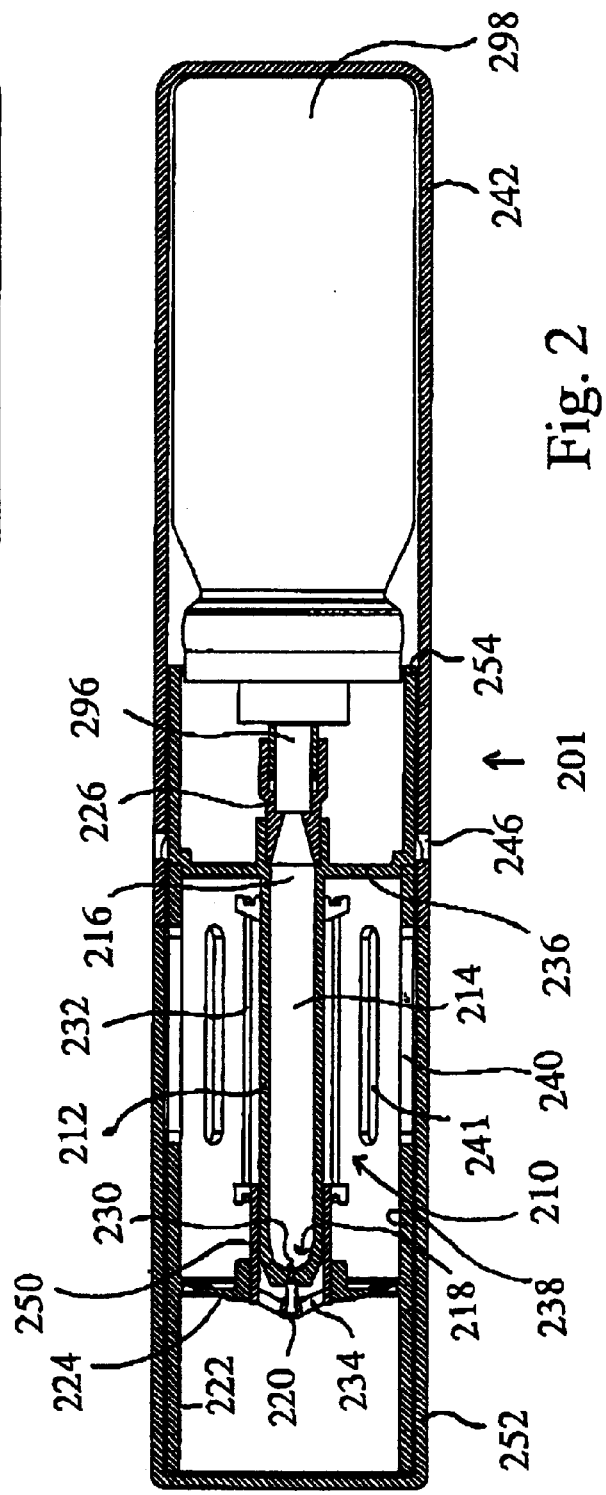
FIG. 2 is a scale drawing of a cross section of a preferred embodiment of the present invention.

FIG. 2 is a scale drawing of a cross section of a device 201. The device 201, adapted for inhalation of a drug from a gas canister 298 by a person suffering from asthma or bronchospasm, comprises a gas container 210 with at least one wall 212. The wall 212 surrounds a gas containment chamber 214. The gas container 210 further has an inlet 216, adapted for connection to an outlet or nozzle 296 of the gas canister 298. The gas container 210 is provided with an outlet 218 with an outlet valve 220. The gas containment chamber 214 may be filled with gas on activation of the gas canister 298. The person may activate the outlet valve 220 on inhalation, whereby inhalation of the gas from the gas containment chamber 214 is possible. The mouthpiece 222, connected to the device 201, allows the person to inhale with the mouth directly from the device. The device 201 is provided with a removable spacer 228 for the mouthpiece 222, whereby the mouthpiece 222 is effectively extended. The device has an exhalation valve 224, which is in flow communication with the mouthpiece. The person may exhale through the device without loss of gas from the gas containment chamber 214. The inlet 216 is connected via receiving means 226 to the nozzle 296 of the gas canister 298. The receiving means 226 may be replaced, inter alia for easy adjustment of the device 201 to different types of gas canisters. Further the device 201 has gas canister holding means 254, for secure mounting of the gas canister. The outlet valve comprises a valve pin 230, spring means 232 and spring attachment means 256. The spring means 232 are connected to the gas container 210 and via the spring attachment means 256 to the valve pin 230. The spring means 232 force the valve pin 230 to close the outlet valve 220 except on inhalation, and allows the outlet valve 220 to open upon inhalation. The device 201 has an outer wall 238 and spacing means 236 for connecting the gas container 210 with the outer wall 238. The outlet valve 220 comprises the exhalation valve 224 with a resilient flap valve. The circumference of the resilient flap valve is in close proximity with the outer wall 238. The resilient flap valve has at least one inhalation opening 234 close to the center. This inhalation opening 234 allows gas to pass from the gas containment chamber to the patient upon inhalation. The device 201 has sliding means 250 around the wall 212 of the gas container 210. The sliding means can slide with respect to the outer surface of the wall 212 of the gas container 210, and is connected to the outlet valve 220, whereby the outlet valve will be held in place upon exhalation and inhalation. The outer wall 238 is shaped as a tube with a diameter substantially equal to the diameter of the gas canister. The outer wall 238 surrounds said inlet and said outlet of the gas container 210, and is connected to the gas container by the spacing means 236, as well as to the mouthpiece 222. The outer wall 238 is provided with a number of openings 240 and 241, situated between said inlet and said outlet of said gas container, whereby gas may escape upon exhalation. The device is further provided with an outer cover 242, which covers the gas canister. When the device is not used for inhalation and/or exhalation, it is provided with removable cover means 252. The cover means protects the outer valve 220 and covers the openings 240 and 241, such that dirt does not enter the device 201.

Generally, all parts of the device are made from plastic. However, for certain parts, other materials are preferred. For the valve pin 230 titanium is preferred, for the spring means 232 rubber bands are preferred, for the resilient flap valve of the exhalation valve 224 silicone is preferred, and for the clip 244 a resilient material such as metal is preferred. The length of the depicted device is about 170 mm.

The strength of the spring means, i.e. the rubber bands, is easily adjusted by choosing it such that a mass of 5 g, hanging freely from the device, is adequate for activating the outlet valve.

The area, $A_1$, of the tip of the pin is less than 0.3 mm$^2$, while the area, $A_2$, of the resilient flap is about 550 mm$^2$. Thus, by appropriate choice of spring means, very high values of OPV parameter may be obtained, e.g. 1500.

Figure 3:
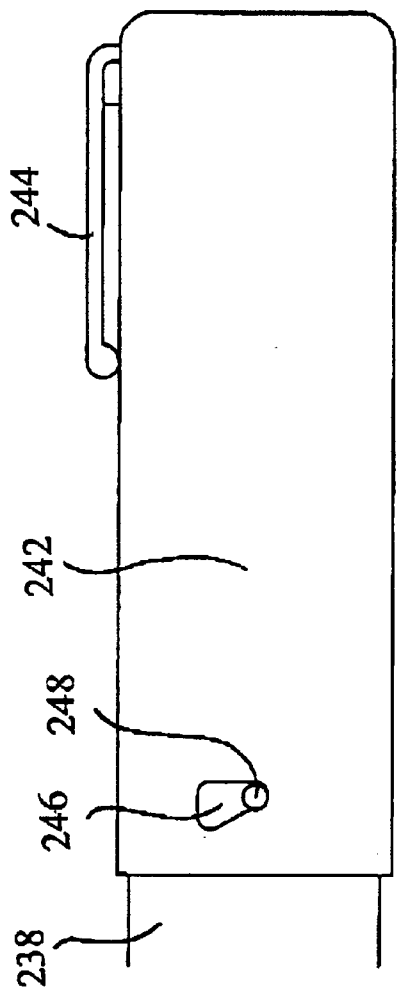
FIG. 3 is a scale drawing seen from the outside of an embodiment of the present device, inter alia depicting the gas canister covering part.

FIG. 3 is a scale drawing seen from the outside of the device. The outer cover 242 conceals the gas canister and part of the outer wall 238. On the outside of the outer cover 242 is placed a clip 244, for fixation of the device to clothes. The outer surfaces of the device are generally cylinder shaped, which means the device mimics a normal thick pen. The outer cover 242 has a triangular shaped elongated opening 246 through which an activation pin 248, attached to the device 201, protrudes. The figure shows the activation pin 248 in the activation position, where at least one dose of drug has been released from the gas canister. By turning the outer cover 242 with respect to the outer wall 238 back and forth, additional doses may be released from the gas canister, because the activation pin 248 engages the elongated opening 246. It is thus possible to effectuate activation of the gas canister 298 by rotation of the outer cover 242 with respect to the outer wall 238.

FIG. 4 is a scale drawing of a section of the cross section shown in FIG. 2, which depicts the construction around the inlet 216 of the gas container. The inlet 216 is in flow communication with connecting part 264, on which is mounted receiving means 226. Inside the receiving means 226 is the nozzle 296 of the gas canister. Sealing means 262 is provided for sealing between the receiving means 226 and the nozzle 296. An O-ring 260 is also provided at the end of the sealing means 262 for improving the sealing and softening the impact of sealing means 262 engaging receiving means 226.

FIG. 5 is a scale drawing of a section of the cross section shown in FIG. 2, which depicts the outlet valve 220. The outlet valve 220 is surrounded by the outer wall 238, and is mounted on sliding means 250, whereby the outlet valve 220 moves with respect to the wall 212 of the gas container. The valve pin 230, mounted in the center of the outlet valve 220, closes the outlet. The exhalation valve 224 is actuated by inhalation and exhalation of the patient, and forces, together with the spring means 232, fixed to the spring attachment means 256, the outlet valve 220 to open upon inhalation and close upon exhalation. The inhalation opening 234 allows gas containing an active drug to pass to the patient upon inhalation.

FIG. 6 shows a detail from the scale drawing of FIG. 3, depicting the triangular shape of the elongated opening 246, with an activation pin 248 sticking through. This will help a person with impaired vision in ascertaining the activation state of the gas canister, as the position of the activation pin 248 may be felt with a finger. In the preferred embodiment, the device is provided with two such activations pins, opposite each other, on each side of the device.

In order to mount the outer cover 242 for covering the gas canister 298, the outer cover 242, made of resilient plastic, is preferably pressed slightly close to its open end, thereby changing the form of the open end from having a circular cross section to being slightly oval, whereby the outer cover 242 may slide above the activation pin 248, and be locked in place upon release of the pressure.

As this preferred embodiment is only intended to be used once and then discarded, it is designed to make it cumbersome to exchange the gas canister, after the gas canister has been mounted.

The foregoing description is only intended to elucidate, not limit, the present invention.

What is claimed is:

1. A device for the inhalation of at least one drug; from a gas canister having a nozzle the device comprising:
    a gas container including
        at least one wall, the wall surrounding a gas containment chamber adapted to contain gas at a pressure larger than atmospheric pressure,
        an inlet adapted for connection to a nozzle of a gas canister, and
        an outlet with an outlet valve adapted to allow inhalation of gas from the device through the outlet;
    wherein the outlet valve is adapted to be activated by the inhalation of the person independent of the activation of the gas canister, wherein the device comprises an outer wall shaped as a tube, the outer wall surrounding the inlet and the outlet of the gas container, and the device comprising spacing means for connecting the gas container with the outer wall, wherein the outer wall is provided with at least one opening situated between the inlet and the outlet of the gas container, for allowing air to be let out of the device upon exhalation.

2. The device according to claim 1 further comprising a mouthpiece adapted to allow inhalation of gas from the mouthpiece, the mouthpiece being in flow communication with the outlet valve.

3. The device according to claim 2 further comprising a removable spacer for the mouthpiece, the spacer allowing extending the mouthpiece on mounting.

4. The device according to claim 2 further comprising an exhalation valve, wherein the mouthpiece is in flow communication with the exhalation valve, allowing exhalation through the mouthpiece.

5. The device according to claim 2, wherein the outer wall has a diameter substantially equal to the diameter of the gas canister.

6. The device according to claim 1, wherein the inlet is provided with receiving means being connectable to the inlet of the gas container, wherein the receiving means is adapted to receive the nozzle of the gas canister.

7. The device according to claim 1, having gas canister holding means connected to the gas container, the gas canister holding means being adapted to receiving and holding the gas canister.

8. The device according to claim 1;
wherein the atmosphere surrounding said the device has a pressure, $P_{atm}$; the outlet valve experiences an inner pressure from the gas containment chamber before activation of the outlet valve, $P_{ca}$; and the outlet valve experiences an outer pressure before activation of the outlet valve, $P_{ma}$;
wherein the outlet valve is adapted to have an outlet valve parameter, OVP, larger than 1; the outlet valve parameter, OVP, being defined by the condition for activation, B, of the outlet valve:

$$B: |P_{ca}-P_{atm}|-OVP|P_{atm}-P_{ma}|<0 \text{ atm};$$

such that the outlet valve of the container is activated when the condition for activation, B, is fulfilled.

9. The device according to claim 8, wherein the outlet valve is adapted to have an outlet valve parameter, OVP, larger than a number selected among the group consisting of 20; 15; 10; 8; 6; 5; 4; 3; 2.5; 2; 1.5; 1.4; 1.3; 1.2 and 1.1.

10. The device according to claim 1, wherein said the outlet valve comprises a valve pin, spring means and spring attachment means; the spring means being connected to the gas container, and via the spring attachment means being connected to and forcing the valve pin to close the outlet valve except on inhalation, and allowing the outlet valve to open upon inhalation.

11. The device according to claim 1, wherein the gas in the gas containment chamber exerts a force on the outlet valve on a first area, $A_1$, and the outer pressure exerts a force on the outlet valve on a second area, $A_2$, the first area being smaller than the second area; $A_1<A_2$.

12. The device according to claim 11, wherein the ratio $A_2/A_1$, between the second area, $A_2$, and said the first area, $A_1$, is larger than a number selected among the group consisting of 5000; 2000; 1500; 1000; 500; 300; 100; 50; 30; 20; 10; 5; 4; 3; 2 and 1.5.

13. The device according to claim 1, the device comprising an outer wall and spacing means for connecting the gas container with the outer wall; wherein the outlet valve comprises an exhalation valve having a resilient flap valve with a circumference in close proximity to the outer wall, the resilient flap valve being adapted to allow air to be exhaled without activation of the outlet valve, and allowing activation of the outlet valve upon inhalation; and the resilient flap valve having an inhalation opening through which gas from the gas containment chamber may pass, allowing gas to flow from the gas containment chamber to the patient upon inhalation.

14. The device according to claim 13, wherein the resilient flap valve allows air to flow substantially freely on exhalation, while only allowing a limited stream of air to pass between the circumference of the resilient flap valve and the inner surface of the outer wall upon inhalation.

15. The device according to claim 1, the device comprising sliding means connected to the outlet valve, the sliding means being adapted to slide with respect to the outer surface of the wall of the gas container upon activation of the outlet valve.

16. The device according to claim 1, wherein the outer cover covers at least part of the bottom part of the gas canister, wherein the cover is adapted to fit the gas canister and allow movement of the outer cover with respect to the gas container, so that the gas container may be activated by movement of the cover.

17. The device according to claim 16, wherein the gas canister is activated by rotation of the outer cover with respect to the gas container.

18. The device according to claim 17, wherein the outer cover comprises an elongated opening, the elongated opening having at least a part slanted with respect to the longitudinal direction of the gas canister, and the device further comprises an activation pin connected to the gas container, the pin engaging said the elongated opening so that rotation of the outer cover with respect to the gas container activates the gas canister.

19. The device according to claim 1, wherein the gas containment chamber is adapted to contain gas at a pressure larger than a pressure selected among the group consisting of 1.05; 1.1; 1.2; 1.3; 1.5; 1.6; 1.7; 1.8; 1.9; 2; 2.5 and 3 atm.

* * * * *